US011026805B2

(12) United States Patent
Suddaby

(10) Patent No.: US 11,026,805 B2
(45) Date of Patent: Jun. 8, 2021

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 71 days.

(21) Appl. No.: 16/525,801

(22) Filed: Jul. 30, 2019

(65) Prior Publication Data

US 2021/0030562 A1 Feb. 4, 2021

(51) Int. Cl.
*A61F 2/44* (2006.01)
*A61F 2/30* (2006.01)

(52) U.S. Cl.
CPC ........ *A61F 2/4465* (2013.01); *A61F 2/30771* (2013.01); *A61F 2002/30471* (2013.01); *A61F 2002/30484* (2013.01); *A61F 2002/30601* (2013.01); *A61F 2002/30904* (2013.01)

(58) Field of Classification Search
CPC ............................................. A61F 2/4455–447
See application file for complete search history.

(56) References Cited

U.S. PATENT DOCUMENTS

| 5,390,683 | A | * | 2/1995 | Pisharodi | ................ | A61F 2/446 128/898 |
| 5,483,463 | A | | 1/1996 | Qin et al. | | |
| 5,505,732 | A | | 4/1996 | Michelson | | |
| 5,653,761 | A | | 8/1997 | Pisharodi | | |
| 5,653,762 | A | | 8/1997 | Pisharodi | | |
| 5,665,122 | A | | 9/1997 | Kambin | | |
| 5,683,463 | A | | 11/1997 | Godefroy et al. | | |
| 6,126,689 | A | * | 10/2000 | Brett | ..................... | A61F 2/4455 623/17.16 |
| 6,159,244 | A | * | 12/2000 | Suddaby | ............... | A61F 2/4611 623/17.11 |
| 6,174,334 | B1 | | 1/2001 | Suddaby | | |
| 6,332,895 | B1 | | 12/2001 | Suddaby | | |
| 7,044,971 | B2 | | 5/2006 | Suddaby | | |
| 7,083,650 | B2 | * | 8/2006 | Moskowitz | ............ | A61F 2/441 606/247 |
| 7,318,839 | B2 | | 1/2008 | Malberg et al. | | |
| 7,465,317 | B2 | | 12/2008 | Malberg et al. | | |
| 8,152,837 | B2 | | 4/2012 | Altarac et al. | | |
| 8,241,358 | B2 | * | 8/2012 | Butler | .................. | A61F 2/4611 623/17.11 |
| 8,361,148 | B2 | | 1/2013 | Malberg et al. | | |

(Continued)

FOREIGN PATENT DOCUMENTS

WO    WO2009/064787    5/2009

*Primary Examiner* — Eduardo C Robert
*Assistant Examiner* — Steven J Cotroneo
(74) *Attorney, Agent, or Firm* — Simpson & Simpson, PLLC; Michael Nicholas Vranjes

(57) ABSTRACT

An expandable intervertebral fusion implant, including a first vertical member, an inferior component, including first longitudinal member pivotably connected to the first vertical member, and a second longitudinal member pivotably connected to the first vertical member, and a superior component, including a third longitudinal member pivotably connected to the first vertical member, and a fourth longitudinal member pivotably connected to the first vertical member, wherein the superior component is operatively arranged to displace relative to the inferior component.

20 Claims, 12 Drawing Sheets

(56) References Cited

U.S. PATENT DOCUMENTS

| | | | |
|---|---|---|---|
| 8,628,577 B1 * | 1/2014 | Jimenez | A61F 2/442 623/17.15 |
| 8,845,730 B2 | 9/2014 | de Villiers et al. | |
| 8,986,384 B2 | 3/2015 | Malberg et al. | |
| 9,039,742 B2 | 5/2015 | Altarac et al. | |
| 9,072,549 B2 | 7/2015 | Butler et al. | |
| 9,351,846 B2 | 5/2016 | De Villiers et al. | |
| 9,387,016 B2 | 7/2016 | Okamoto et al. | |
| 9,408,710 B2 * | 8/2016 | Purcell | A61F 2/447 |
| 9,463,099 B2 | 10/2016 | Levy et al. | |
| 9,675,466 B2 * | 6/2017 | Overes | A61F 2/4425 |
| 9,901,460 B2 * | 2/2018 | Goel | A61F 2/4455 |
| 9,956,090 B2 | 5/2018 | Baynham | |
| 10,143,501 B2 | 12/2018 | Northcutt et al. | |
| 10,322,005 B1 * | 6/2019 | Suddaby | A61F 2/4405 |
| 10,327,912 B1 * | 6/2019 | Suddaby | A61F 2/4455 |
| 2004/0044411 A1 * | 3/2004 | Suddaby | A61F 2/4455 623/17.15 |
| 2006/0241643 A1 * | 10/2006 | Lim | A61B 17/025 606/90 |
| 2007/0123987 A1 | 5/2007 | Bernstein | |
| 2013/0123927 A1 | 5/2013 | Malandain | |
| 2013/0197642 A1 * | 8/2013 | Ernst | A61F 2/442 623/17.16 |
| 2013/0310939 A1 * | 11/2013 | Fabian | A61F 2/4455 623/17.16 |
| 2014/0018922 A1 * | 1/2014 | Marino | A61F 2/447 623/17.16 |
| 2014/0194992 A1 * | 7/2014 | Medina | A61F 2/4611 623/17.16 |
| 2016/0296339 A1 | 10/2016 | de Villiers et al. | |
| 2016/0324654 A1 | 11/2016 | Loebl et al. | |
| 2016/0331542 A1 * | 11/2016 | Faulhaber | A61F 2/447 |
| 2017/0100256 A1 | 4/2017 | Bootwala et al. | |
| 2017/0231778 A1 | 8/2017 | Overes et al. | |
| 2017/0231781 A1 | 8/2017 | Kraemer | |
| 2018/0280153 A1 | 10/2018 | Eastlack et al. | |
| 2019/0021873 A1 | 1/2019 | Dmuschewsky | |
| 2019/0053912 A1 * | 2/2019 | Suddaby | A61F 2/447 |

* cited by examiner

EXPANDABLE INTERVERTEBRAL FUSION IMPLANT

FIELD

The present disclosure relates to orthopedic surgery, and more particularly to an expandable and deployable intervertebral fusion implant capable of being placed within an intervertebral disc space and expanded in vertical and lateral dimensions.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, to transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

U.S. Pat. No. 5,505,732 (Michelson), U.S. Pat. No. 5,653,761 (Pisharodi I), U.S. Pat. No. 5,665,122 (Kambin), and U.S. Pat. No. 5,683,463 (Godefroy et al.) disclose different prior art spinal implants. The implant disclosed in U.S. Pat. No. 5,483,463 (Qin et al.) is hollow and tubular, with communicating windows in the top and bottom surfaces. External ribs, which may be serrated, stabilize the implant once it is inserted between the vertebrae. Kambin discloses an intervertebral cage that is expandable by a wedging mechanism. The degree of expansion is rather limited. However, Michelson and U.S. Pat. No. 5,653,762 (Pisharodi II) disclose shaft-type tools used for installing implants. The prior art devices do not enable one to achieve great ranges of implant height.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

U.S. Pat. No. 6,174,334 (Suddaby I) and U.S. Pat. No. 6,332,895 (Suddaby II) disclose expandable cages using a ratcheting mechanism in the perimeter to achieve expansion, as well as an installation tool used to expand the expandable cages, which patents are incorporated by reference in their entireties.

Thus, there is a long-felt need for an expandable and deployable intervertebral fusion implant capable of being placed within an intervertebral disc space and expanded in vertical and lateral dimensions.

SUMMARY

According to aspects illustrated herein, there is provided an expandable intervertebral fusion implant, comprising a first vertical member, an inferior component, including first longitudinal member pivotably connected to the first vertical member, and a second longitudinal member pivotably connected to the first vertical member, and a superior component, including a third longitudinal member pivotably connected to the first vertical member, and a fourth longitudinal member pivotably connected to the first vertical member, wherein the superior component is operatively arranged to displace relative to the inferior component.

According to aspects illustrated herein, there is provided an expandable intervertebral fusion implant, comprising a vertical member, an inferior component, including first longitudinal member pivotably connected to the vertical member and including a first plurality of teeth, and a second longitudinal member pivotably connected to the vertical member and including a second plurality of teeth, and a superior component, including a third longitudinal member pivotably connected to the vertical member and including a third plurality of teeth, and a fourth longitudinal member pivotably connected to the vertical member and including a fourth plurality of teeth, wherein the superior component is operatively arranged to displace in a first direction relative to the inferior component.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Adverting now to the figures, and as described previously, FIGS. 1-6 depict various parts and sections of spinal anatomy.

Figure 1:
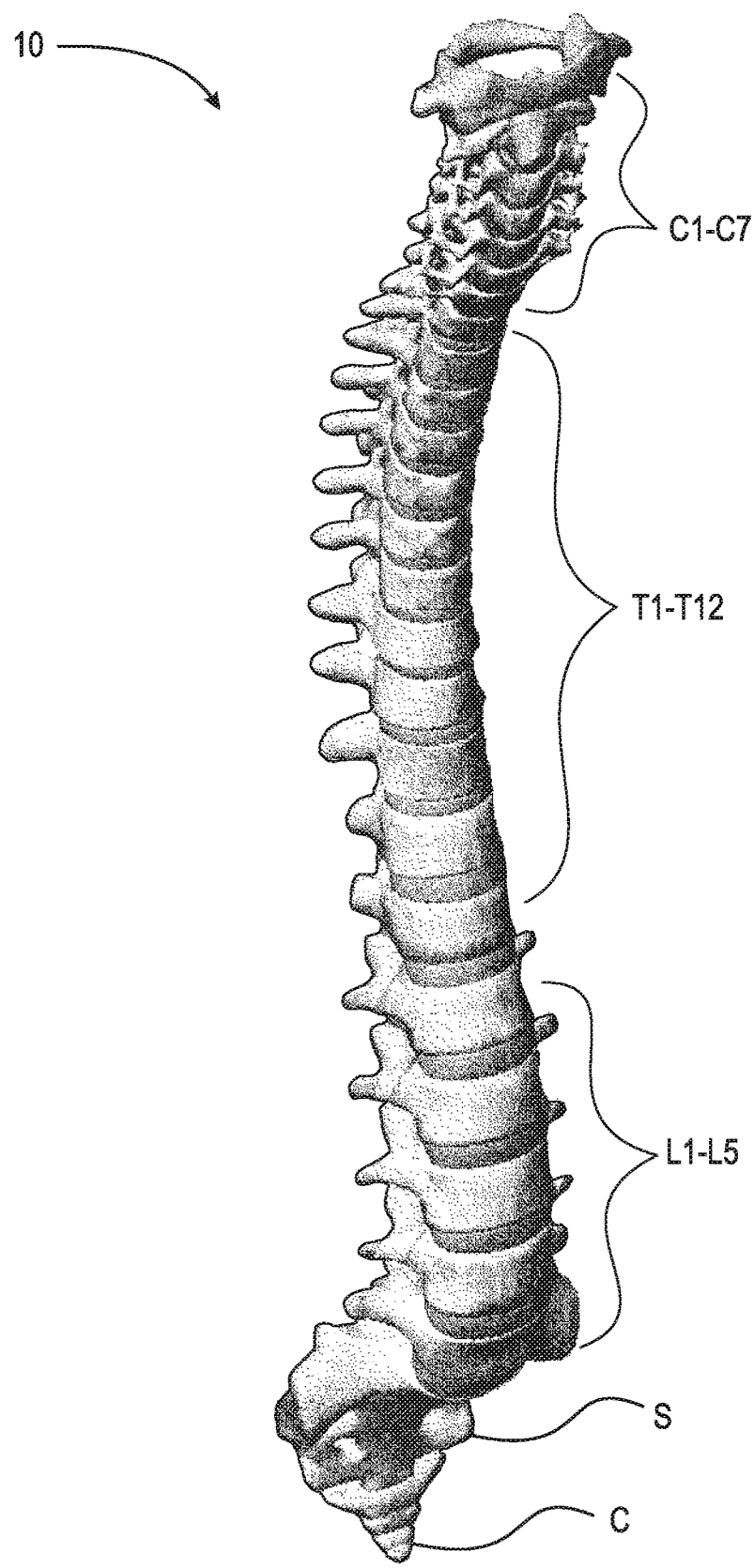
FIG. 1 is an anterior perspective view of a spinal column.
Figure 2:
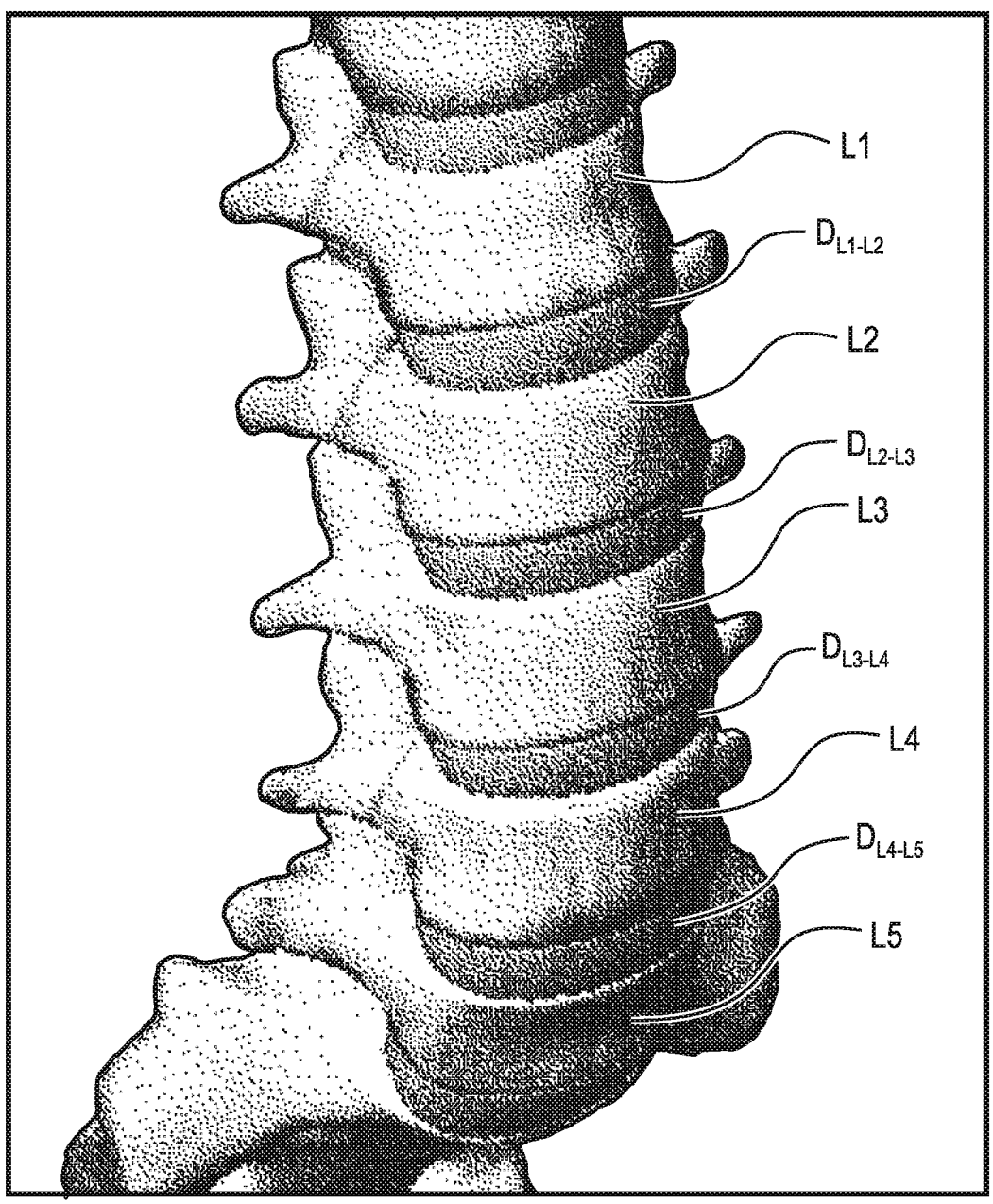
FIG. 2 is an anterior perspective view of the lumbar section of the spinal column shown in FIG. 1.
Figure 3:
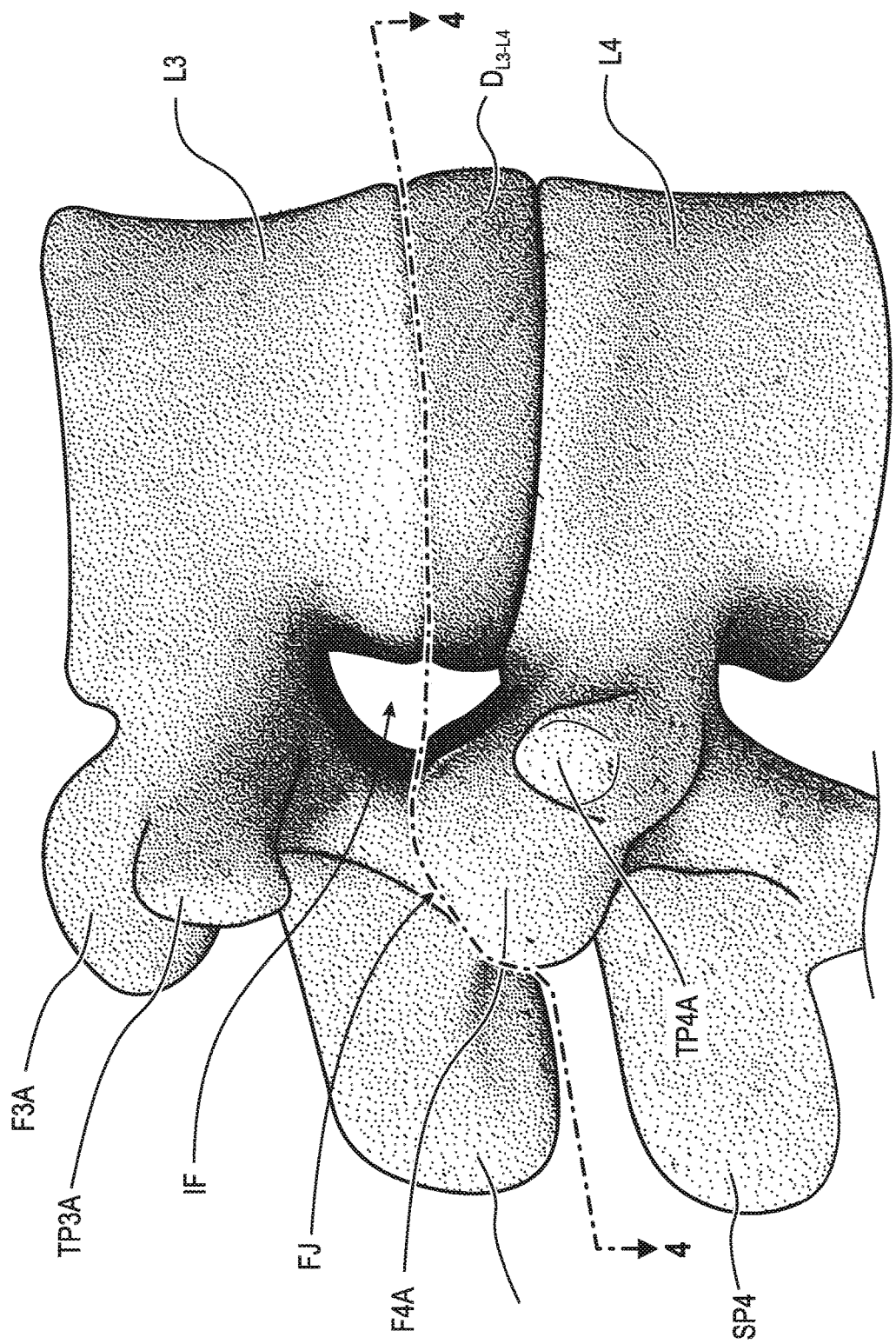
FIG. 3 is a lateral perspective view of two vertebrae, a disc, and related spinal anatomy.
Figure 4:
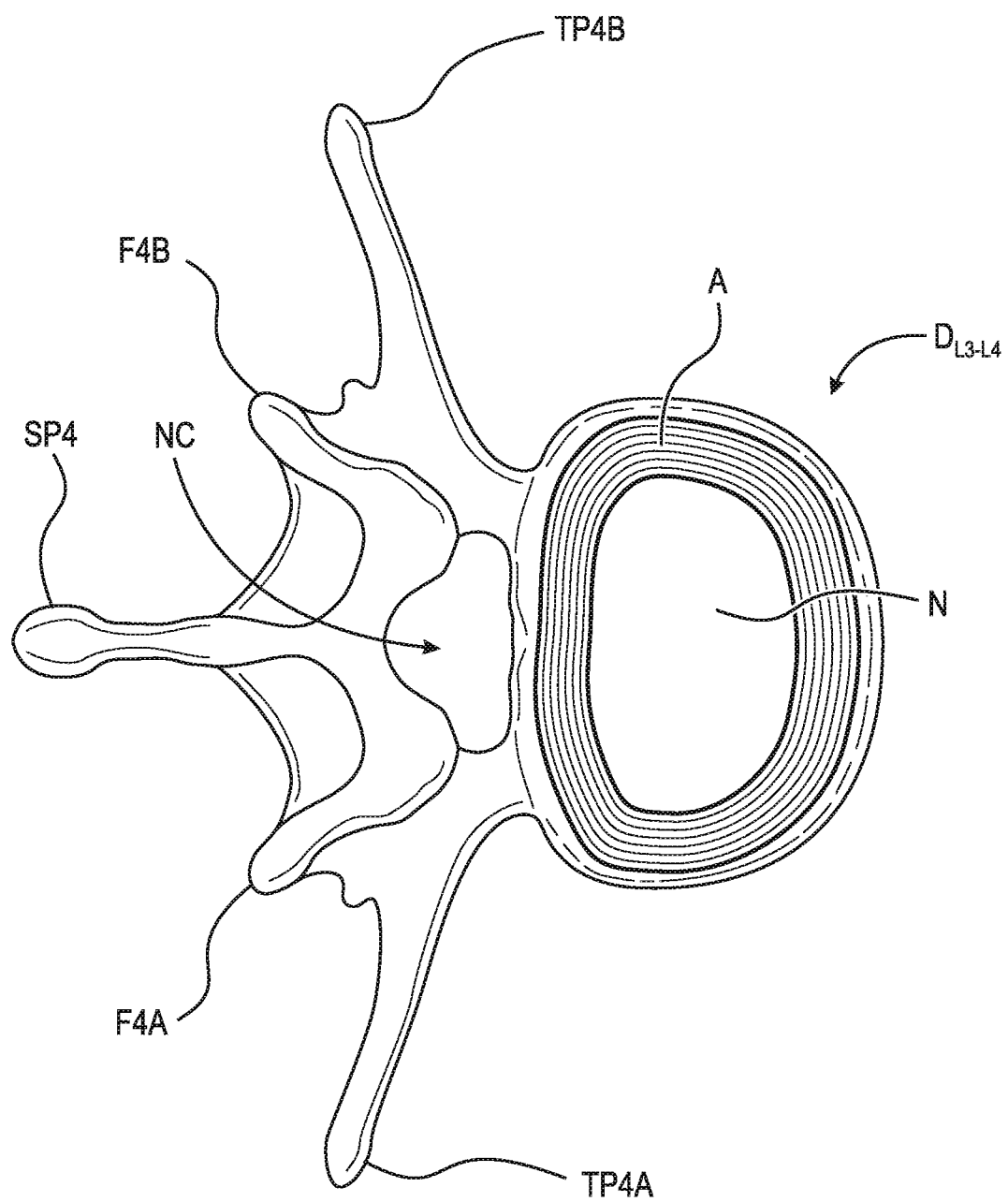
FIG. 4 is a top view of a section of the spinal column, taken generally along line 4-4 in FIG. 3.
Figure 5:
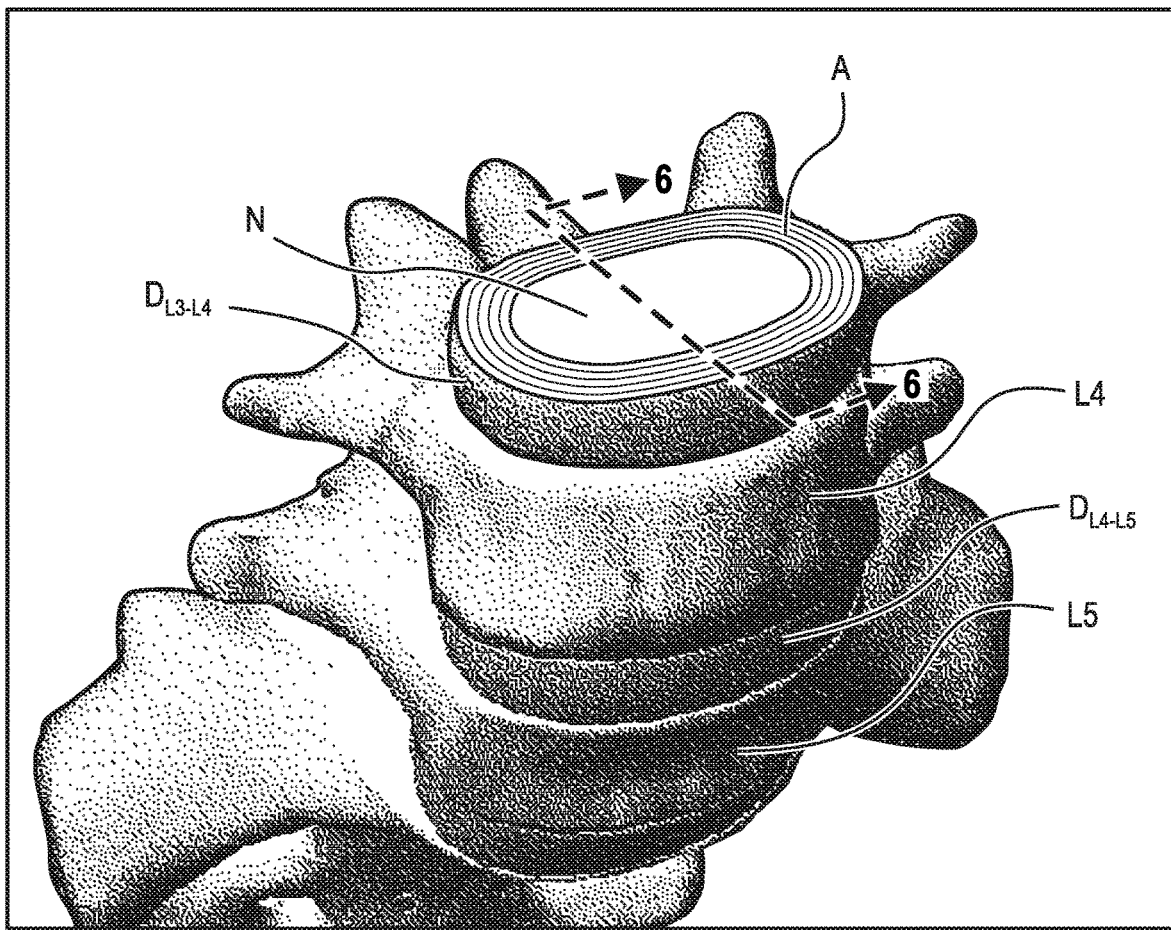
FIG. 5 is an enlarged anterior perspective view of the spinal column shown in FIG. 2, except with the top vertebra and all other structure above the top vertebra removed.
Figure 6:
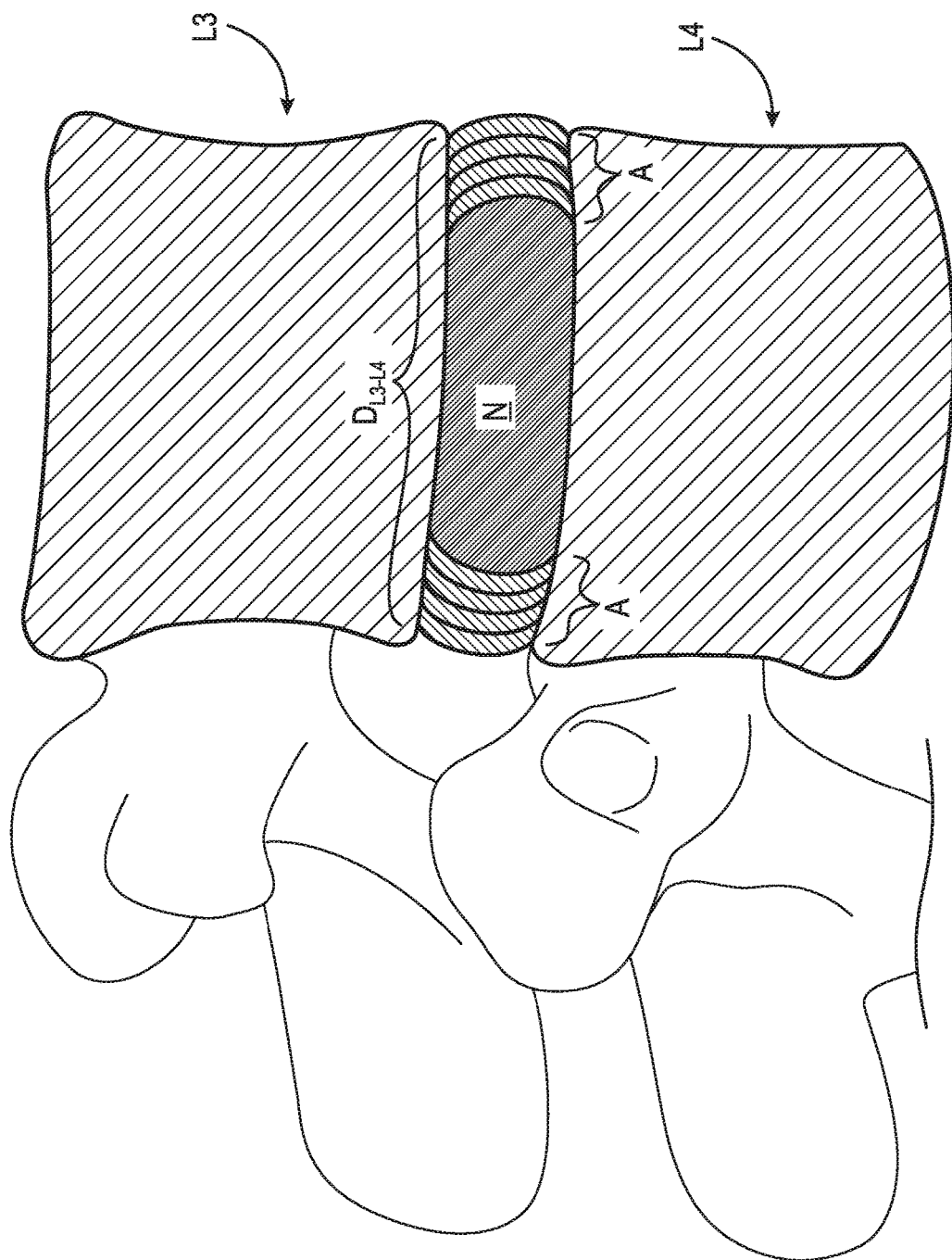
FIG. 6 is a partial cross-sectional view of the top and bottom vertebrae and disc, taken generally along line 6-6 in FIG. 5.
Figure 7:
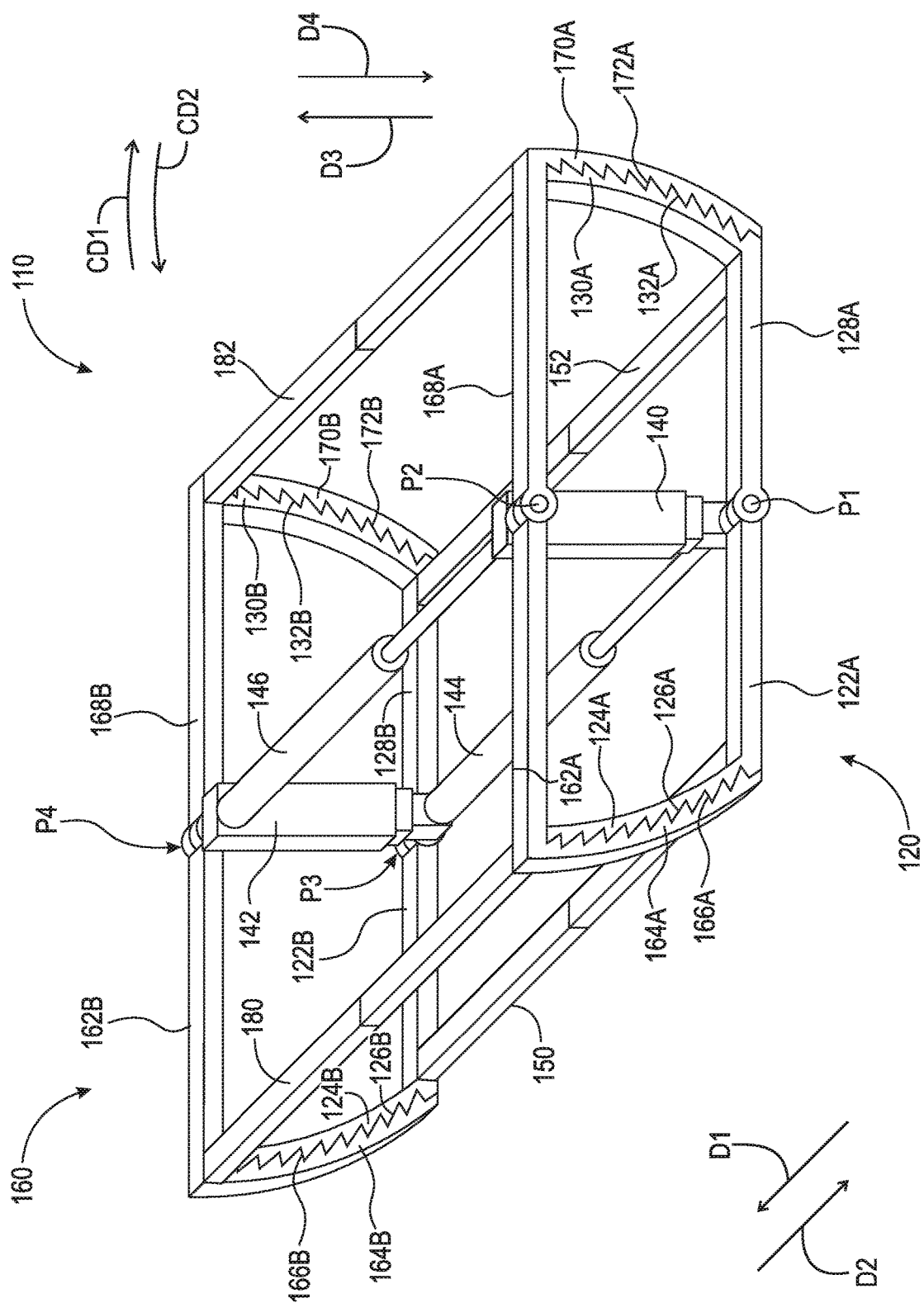
FIG. 7 is a front perspective view of an expandable intervertebral fusion implant, in a collapsed state.
Figure 8:
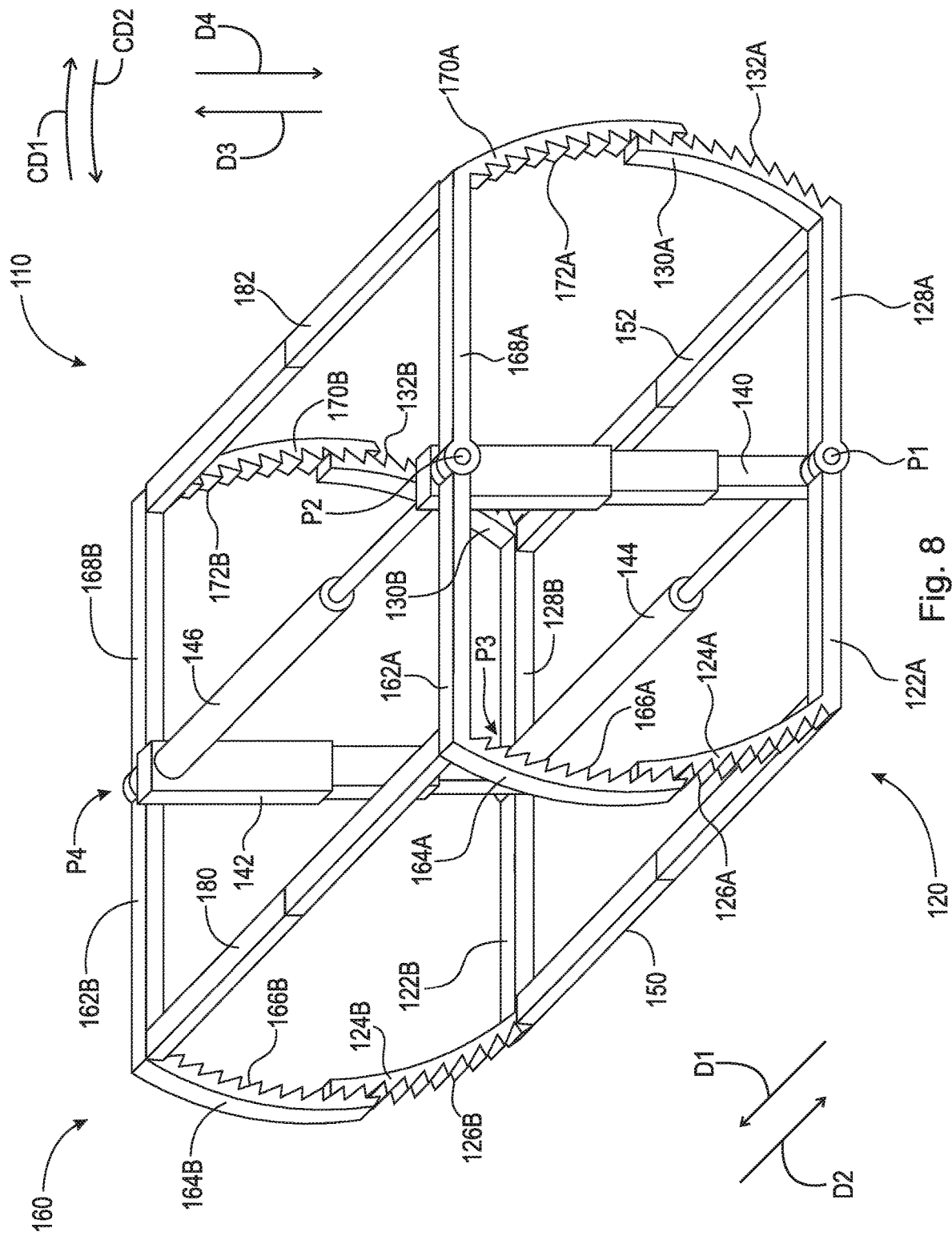
FIG. 8 is a front perspective view of the expandable intervertebral fusion implant shown in FIG. 7, in an expanded state.
Figure 9:
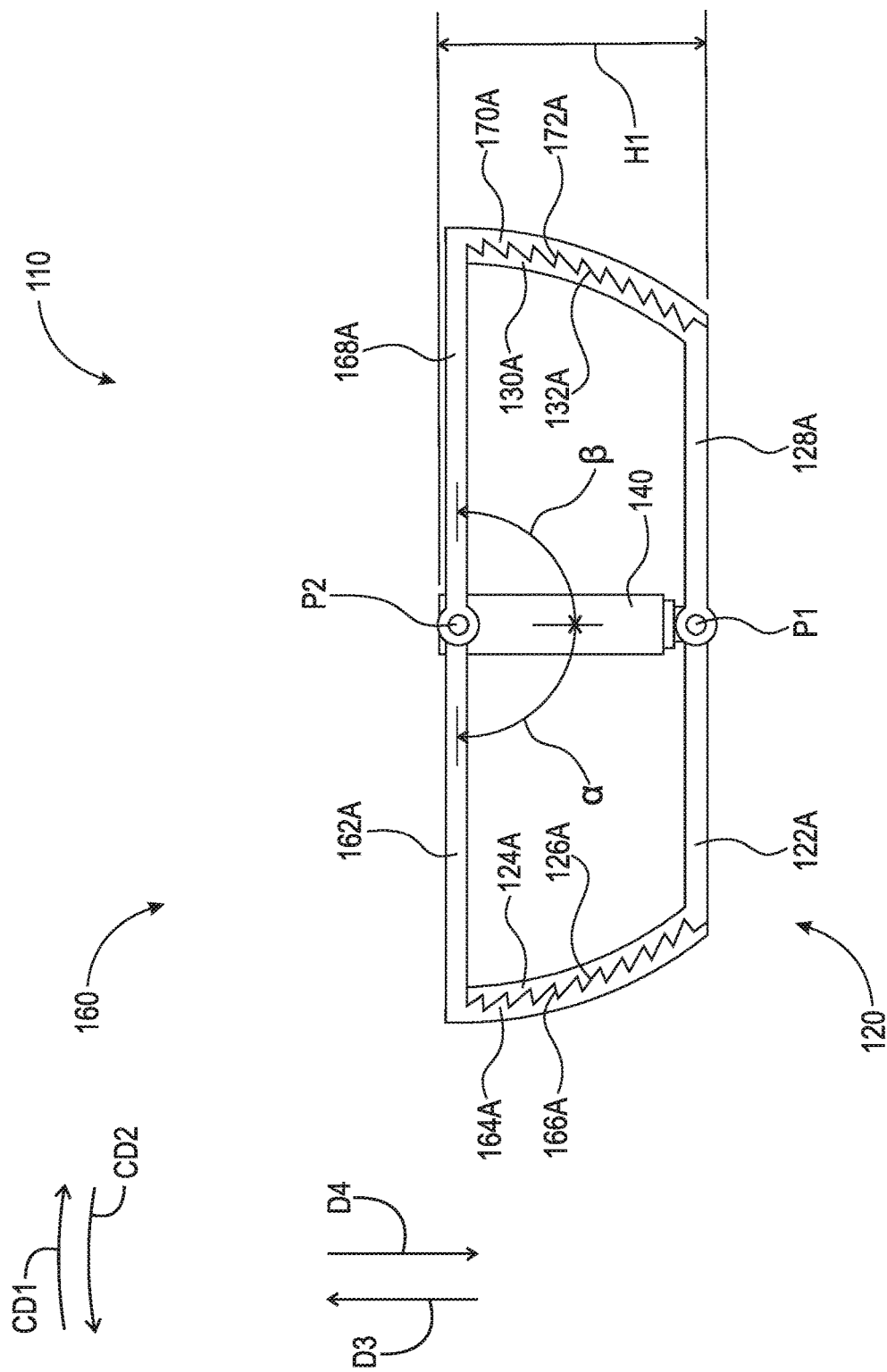
FIG. 9 is a front elevational view of the expandable intervertebral fusion implant shown in FIG. 7.
Figure 10:
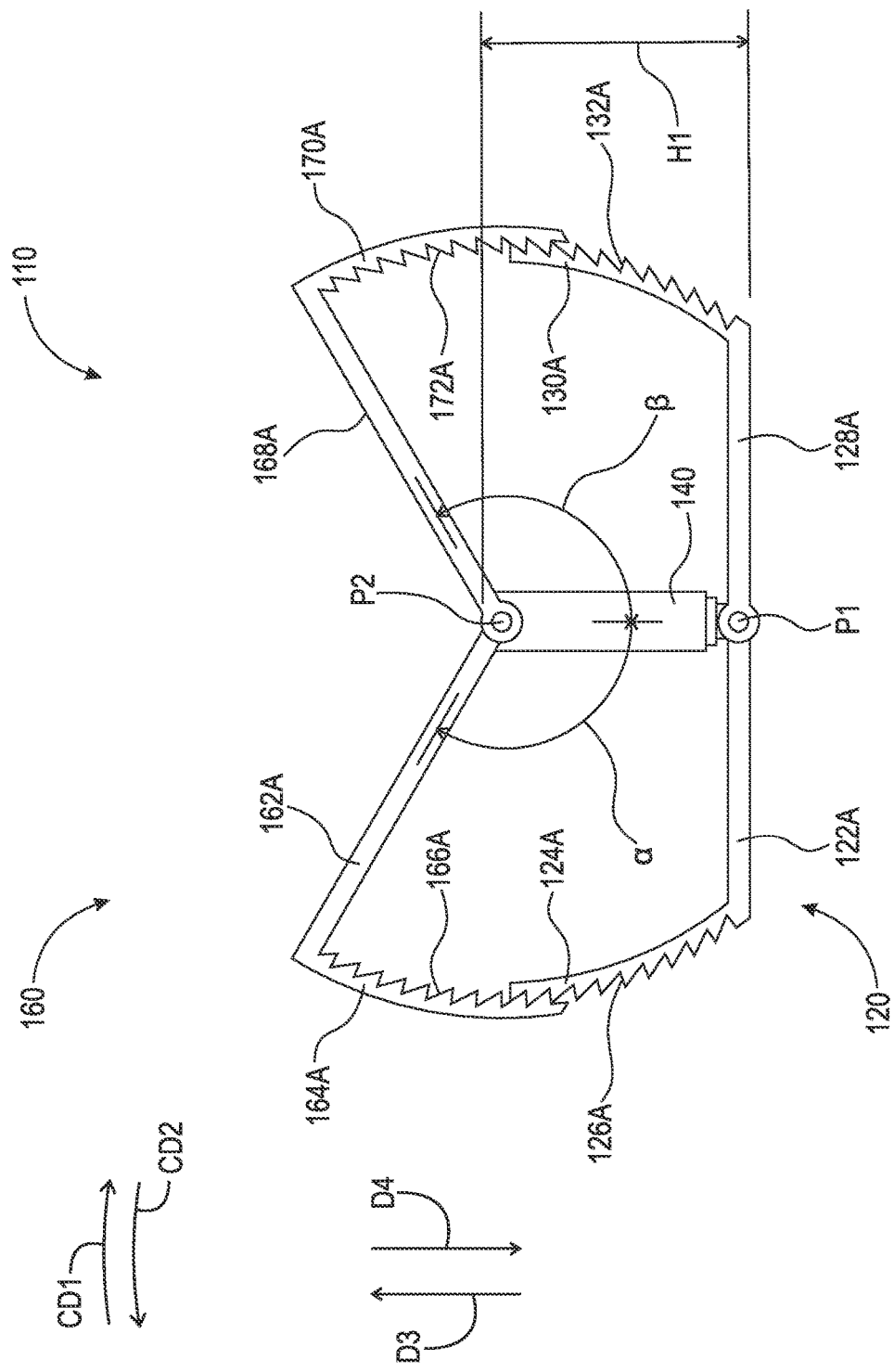
FIG. 10 is a front elevational view of the expandable intervertebral fusion implant shown in FIG. 7, in a partial expanded state.
Figure 11:
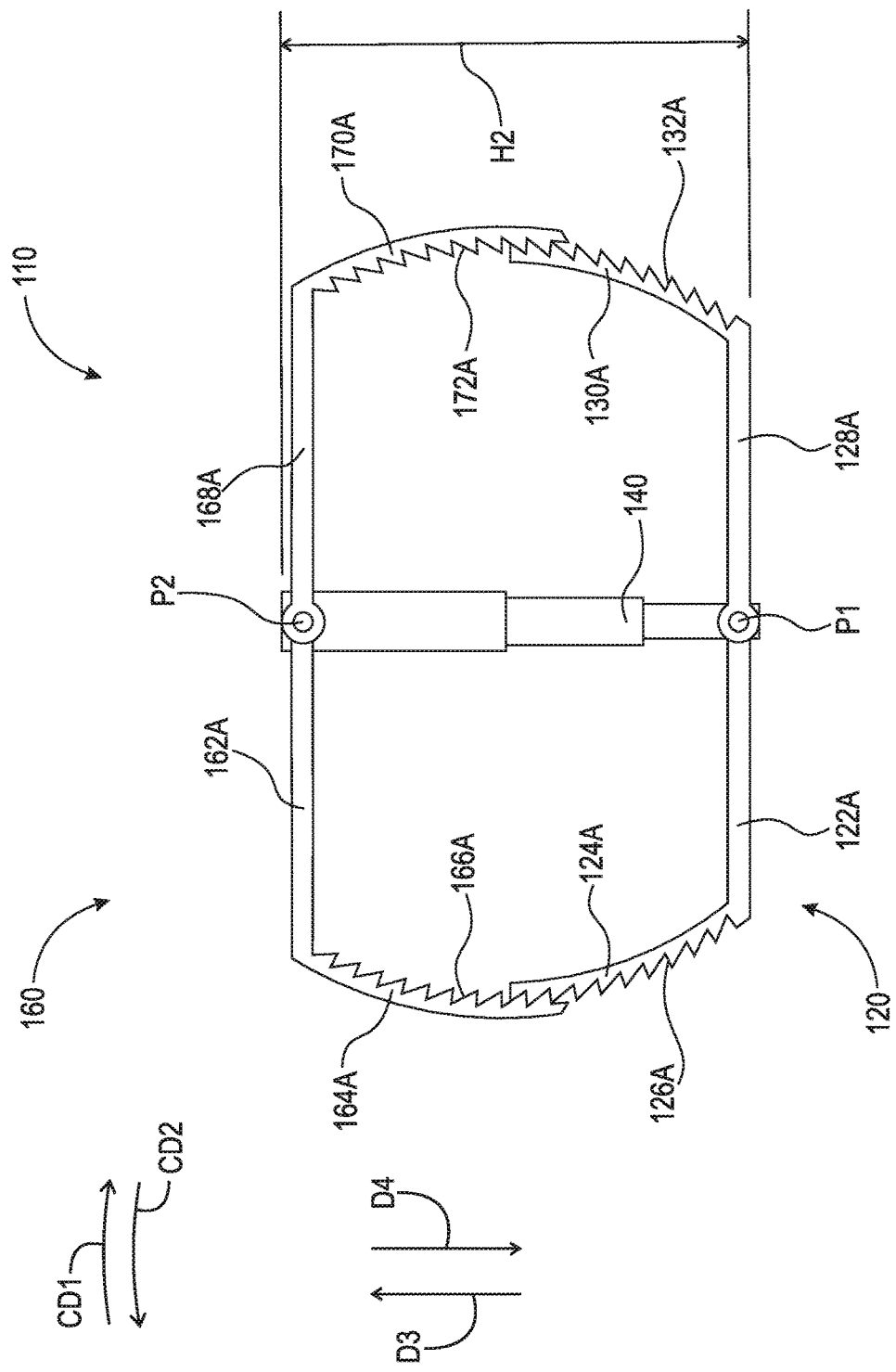
FIG. 11 is a front elevational view of the expandable intervertebral fusion implant shown in FIG. 7, in the expanded state; and, FIG. 12 is an anterior perspective view of a spinal column including the expandable intervertebral fusion implant shown in FIG. 7, in the expanded state.

FIG. 7 is a front perspective view of expandable intervertebral fusion implant 110, in a collapsed state. FIG. 8 is a front perspective view of expandable intervertebral fusion implant 110, in an expanded state. FIG. 9 is a front elevational view of expandable intervertebral fusion implant 110. FIG. 10 is a front elevational view of expandable intervertebral fusion implant 110 in a partial expanded state. FIG. 11 is a front elevational view of expandable intervertebral fusion implant 110 in the expanded state. Expandable intervertebral fusion implant 110 generally comprises inferior component 120, superior component 160, and at least one vertical member, for example, vertical member 140 and vertical member 142. The following description should be read in view of FIGS. 7-11.

Inferior component 120 comprises longitudinal members 122A-B, longitudinal members 128A-B, and cross-member 150, 152, and 144.

Longitudinal member 122A is pivotably connected to vertical member 140 at a first end. Longitudinal member 122A further comprises leg 124A including plurality of teeth 126A. Leg 124A is connected to longitudinal member 122A at a second end, opposite the first end. In some embodiments, leg 124A is fixedly secured to longitudinal member 122A. In some embodiments, leg 124A is arranged substantially perpendicular to longitudinal member 122A. Longitudinal member 122A is pivotably connected to vertical member 140 via pivot P1. Pivot P1 may comprise a hinge or a pin assembly such that longitudinal member 122A, and leg 124A, is rotatable in circumferential directions CD1 and CD2 with respect to vertical member 140. Teeth 126A are operatively arranged to engage with teeth 166A of leg 164A to lock longitudinal member 162A at a set distance relative to longitudinal member 122A, as will be discussed in greater detail below.

Longitudinal member 128A is pivotably connected to vertical member 140 at a first end. Longitudinal member 128A further comprises leg 130A including plurality of teeth 132A. Leg 130A is connected to longitudinal member 128A at a second end, opposite the first end. In some embodiments, leg 130A is fixedly secured to longitudinal member 128A. In some embodiments, leg 130A is arranged substantially perpendicular to longitudinal member 128A. Longitudinal member 128A is pivotably connected to vertical member 140 via pivot P1. Pivot P1 may comprise a hinge or a pin assembly such that longitudinal member 128A, and leg 130A, is rotatable in circumferential directions CD1 and CD2 with respect to vertical member 140. Teeth 132A are operatively arranged to engage with teeth 172A of leg 170A to lock longitudinal member 168A at a set distance relative to longitudinal member 128A, as will be discussed in greater detail below.

Longitudinal member 122B is pivotably connected to vertical member 142 at a first end. Longitudinal member 122B further comprises leg 124B including plurality of teeth 126B. Leg 124B is connected to longitudinal member 122B at a second end, opposite the first end. In some embodiments, leg 124B is fixedly secured to longitudinal member 122B. In some embodiments, leg 124B is arranged substantially perpendicular to longitudinal member 122B. Longitudinal member 122B is pivotably connected to vertical member 142 via pivot P3. Pivot P3 may comprise a hinge or a pin assembly such that longitudinal member 122B, and leg 124B, is rotatable in circumferential directions CD1 and CD2 with respect to vertical member 142. Teeth 126B are operatively arranged to engage with teeth 166B of leg 164B to lock longitudinal member 162B at a set distance relative to longitudinal member 122B, as will be discussed in greater detail below. In the embodiment shown, longitudinal member 122B is connected to longitudinal member 122A via cross-member 150. Cross-member 150 provides stability to inferior component 120 and requires that longitudinal members 122A-B circumferentially displace at the same rate and measure. In some embodiments, cross-member 150 comprises a plurality of telescoping members to allow expandable intervertebral fusion implant 110 to laterally expand and collapse. For example, longitudinal member 122B may displace in directions D1 and D2 with respect to longitudinal member 122A. It should be appreciated that in some embodiments, longitudinal member 122B is not connected to longitudinal member 122A, such that longitudinal member 122B is independently displaceable relative to longitudinal member 122A and vice versa.

Longitudinal member 128B is pivotably connected to vertical member 142 at a first end. Longitudinal member 128B further comprises leg 130B including plurality of teeth 132B. Leg 130B is connected to longitudinal member 128B at a second end, opposite the first end. In some embodiments, leg 130B is fixedly secured to longitudinal member 128B. In some embodiments, leg 130B is arranged substantially perpendicular to longitudinal member 128B. Longitudinal member 128B is pivotably connected to vertical member 142 via pivot P3. Pivot P3 may comprise a hinge or a pin assembly such that longitudinal member 128B, and leg 130B, is rotatable in circumferential directions CD1 and CD2 with respect to vertical member 142. Teeth 132B are operatively arranged to engage with teeth 172B of leg 170B to lock longitudinal member 168B at a set distance relative to longitudinal member 128B, as will be discussed in greater detail below. In the embodiment shown, longitudinal member 128B is connected to longitudinal member 128A via cross-member 152. Cross-member 152 provides stability to inferior component 120 and requires that longitudinal members 128A-B circumferentially displace at the same rate and measure. In some embodiments, cross-member 152 comprises a plurality of telescoping members to allow expandable intervertebral fusion implant 110 to laterally expand and collapse. For example, longitudinal member 122B may displace in directions D1 and D2 with respect to longitudinal member 122A. It should be appreciated that in some embodiments, longitudinal member 128B is not connected to longitudinal member 128A, such that longitudinal member 128B is independently displaceable relative to longitudinal member 128A and vice versa.

Superior component 160 comprises longitudinal members 162A-B, longitudinal members 168A-B, and cross-member 180, 182, and 146.

Longitudinal member 162A is pivotably connected to vertical member 140 at a first end. Longitudinal member 162A further comprises leg 164A including plurality of teeth 166A. Leg 164A is connected to longitudinal member 162A at a second end, opposite the first end. In some embodiments, leg 164A is fixedly secured to longitudinal member 162A. In some embodiments, leg 164A is arranged substantially perpendicular to longitudinal member 162A. Longitudinal member 162A is pivotably connected to vertical member 140 via pivot P2. Pivot P2 may comprise a hinge or a pin assembly such that longitudinal member 162A, and leg 164A, is rotatable in circumferential directions CD1 and CD2 with respect to vertical member 140. Teeth 166A are operatively arranged to engage with teeth 126A of leg 164A to lock longitudinal member 162A at a set distance relative to longitudinal member 122A. The engagement of teeth 166A with teeth 126A allows longitudinal member 162A to displace relative to longitudinal member 122A in circumferential direction CD1 but not CD2 (and also allows longitudinal member 122A to displace relative to longitudinal member 162A in circumferential direction CD2 but not CD1). In other words, the engagement of teeth 166A and 126A allows expansion of superior component 160 relative to superior component 120 but restricts contraction or collapse of expandable intervertebral fusion implant 110. In some embodiments, at least one of legs 124A and 164A is at least partially flexible such that, for example, leg 124A may be displaced to disengage teeth 126A from teeth 166A. This would allow longitudinal member 162A to displace in circumferential direction CD2 with respect to CD1. In some embodiments, the engagement of teeth 166A and 126A allows for both expansion and collapse of longitudinal members 162A and 122A.

Longitudinal member 168A is pivotably connected to vertical member 140 at a first end. Longitudinal member 168A further comprises leg 170A including plurality of teeth 172A. Leg 170A is connected to longitudinal member 168A at a second end, opposite the first end. In some embodiments, leg 170A is fixedly secured to longitudinal member 168A. In some embodiments, leg 170A is arranged substantially perpendicular to longitudinal member 168A. Longitudinal member 168A is pivotably connected to vertical member 140 via pivot P2. Pivot P2 may comprise a hinge or a pin assembly such that longitudinal member 168A, and leg 170A, is rotatable in circumferential directions CD1 and CD2 with respect to vertical member 140. Teeth 172A are operatively arranged to engage with teeth 132A of leg 130A to lock longitudinal member 168A at a set distance relative to longitudinal member 128A. The engagement of teeth 172A with teeth 132A allows longitudinal member 168A to displace relative to longitudinal member 128A in circumferential direction CD2 but not CD1 (and also allows longitudinal member 128A to displace relative to longitudinal member 168A in circumferential direction CD1 but not CD2). In other words, the engagement of teeth 172A and 132A allows expansion of superior component 160 relative to superior component 120 but restricts contraction or collapse of expandable intervertebral fusion implant 110. In some embodiments, at least one of legs 130A and 170A is at least partially flexible such that, for example, leg 130A may be displaced to disengage teeth 132A from teeth 172A. This would allow longitudinal member 168A to displace in circumferential direction CD1 with respect to CD2. In some embodiments, the engagement of teeth 172A and 132A allows for both expansion and collapse of longitudinal members 168A and 128A.

Longitudinal member 162B is pivotably connected to vertical member 142 at a first end. Longitudinal member 162B further comprises leg 164B including plurality of teeth 166B. Leg 164B is connected to longitudinal member 162B at a second end, opposite the first end. In some embodiments, leg 164B is fixedly secured to longitudinal member 162B. In some embodiments, leg 164B is arranged substantially perpendicular to longitudinal member 162B. Longitudinal member 162B is pivotably connected to vertical member 142 via pivot P4. Pivot P4 may comprise a hinge or a pin assembly such that longitudinal member 162B, and leg 164B, is rotatable in circumferential directions CD1 and CD2 with respect to vertical member 142. Teeth 166B are operatively arranged to engage with teeth 126B of leg 124B to lock longitudinal member 162B at a set distance relative to longitudinal member 122B. The engagement of teeth 166B with teeth 126B allows longitudinal member 162B to displace relative to longitudinal member 122B in circumferential direction CD1 but not CD2 (and also allows longitudinal member 122B to displace relative to longitudinal member 162B in circumferential direction CD2 but not CD1). In other words, the engagement of teeth 166B and 126B allows expansion of superior component 160 relative to superior component 120 but restricts contraction or collapse of expandable intervertebral fusion implant 110. In some embodiments, at least one of legs 124B and 164B is at least partially flexible such that, for example, leg 124B may be displaced to disengage teeth 126B from teeth 166B. This would allow longitudinal member 162B to displace in circumferential direction CD2 with respect to CD1. In some embodiments, the engagement of teeth 166B and 126B allows for both expansion and collapse of longitudinal members 162B and 122B. In the embodiment shown, longitudinal member 162B is connected to longitudinal member 162A via cross-member 180. Cross-member 180 provides stability to superior component 160 and requires that longitudinal members 162A-B circumferentially displace at the same rate and measure. In some embodiments, cross-member 180 comprises a plurality of telescoping members to allow expandable intervertebral fusion implant 110 to laterally expand and collapse. For example, longitudinal member 162B may displace in directions D1 and D2 with respect to longitudinal member 162A. It should be appreciated that in some embodiments, longitudinal member 162B is not connected to longitudinal member 162A, such that longitudinal member 162B is independently displaceable relative to longitudinal member 162A and vice versa.

Longitudinal member 168B is pivotably connected to vertical member 142 at a first end. Longitudinal member 168B further comprises leg 170B including plurality of teeth 172B. Leg 170B is connected to longitudinal member 168B at a second end, opposite the first end. In some embodiments, leg 170B is fixedly secured to longitudinal member 168B. In some embodiments, leg 170B is arranged substantially perpendicular to longitudinal member 168B. Longitudinal member 168B is pivotably connected to vertical member 142 via pivot P4. Pivot P4 may comprise a hinge or a pin assembly such that longitudinal member 168B, and leg 170B, is rotatable in circumferential directions CD1 and CD2 with respect to vertical member 142. Teeth 172B are operatively arranged to engage with teeth 132B of leg 130B to lock longitudinal member 168B at a set distance relative to longitudinal member 128B. The engagement of teeth 172B with teeth 132B allows longitudinal member 168B to displace relative to longitudinal member 128B in circumferential direction CD2 but not CD1 (and also allows longitudinal member 128B to displace relative to longitudinal member 168B in circumferential direction CD1 but not CD2). In other words, the engagement of teeth 172B and 132B allows expansion of superior component 160 relative to superior component 120 but restricts contraction or collapse of expandable intervertebral fusion implant 110. In some embodiments, at least one of legs 130B and 170B is at least partially flexible such that, for example, leg 130B may be displaced to disengage teeth 132B from teeth 172B. This would allow longitudinal member 168B to displace in circumferential direction CD1 with respect to CD2. In some embodiments, the engagement of teeth 172B and 132B allows for both expansion and collapse of longitudinal members 168B and 128B. In the embodiment shown, longitudinal member 168B is connected to longitudinal member 168A via cross-member 182. Cross-member 182 provides stability to superior component 160 and requires that longitudinal members 168A-B circumferentially displace at the same rate and measure. In some embodiments, cross-member 182 comprises a plurality of telescoping members to allow expandable intervertebral fusion implant 110 to laterally expand and collapse. For example, longitudinal member 168B may displace in directions D1 and D2 with respect to longitudinal member 168A. It should be appreciated that in some embodiments, longitudinal member 168B is not connected to longitudinal member 168A, such that longitudinal member 168B is independently displaceable relative to longitudinal member 168A and vice versa.

Vertical member 140 generally connects superior component 160 to inferior component. Vertical member 140 also provides pivot point P1 to which longitudinal members 122A and 128A are pivotably connected, and pivot point P2 to which longitudinal members 162A and 168A are connected, as was discussed above. In some embodiments, vertical member 140 comprises a plurality of telescoping members to allow expandable intervertebral fusion implant 110 to vertically expand and collapse. For example, longitudinal members 162A and 168A may displace in directions D3 and D4 with respect to longitudinal members 122A and 128A, and vice versa.

Vertical member 142 generally connects superior component 160 to inferior component. Vertical member 140 also provides pivot point P3 to which longitudinal members 122B and 128B are pivotably connected, and pivot point P4 to which longitudinal members 162B and 168B are connected, as was discussed above. In some embodiments, vertical member 142 comprises a plurality of telescoping members to allow expandable intervertebral fusion implant 110 to vertically expand and collapse. For example, longitudinal members 162B and 168B may displace in directions D3 and D4 with respect to longitudinal members 122B and 128B, and vice versa. In the embodiment shown, vertical member 142 is connected to longitudinal member 140 via at least one cross-member, for example, cross-members 144 and 146. Cross-members 144 and 146 provide stability to between longitudinal members 122A-B, 128A-B, 162A-B, and 168A-B, and vertical members 140 and 142. In some embodiments, cross-members 144 and 146 comprise a plurality of telescoping members to allow expandable intervertebral fusion implant 110 to lateral expand and collapse. For example, vertical member 142, and thus longitudinal members 122B, 128B, 162B, and 168B may displace in directions D1 and D2 relative to vertical member 140, and thus longitudinal members 122A, 128A, 162A, and 168A.

In some embodiments, at least one of cross-members 144, 146, 150, 152, 180, and 182 comprise a locking and/or control feature. For example, in some embodiments, cross-member 146 comprises an inner rod including outer threading and an outer rod including inner threading, wherein the inner rod threadably engages the outer rod. As the inner rod is rotated in circumferential direction CD1 with respect to outer rod (or vice versa), cross-member 146 expands. As the inner rod is rotated in circumferential direction CD2 with respect to outer rod (or vice versa), cross-member 146 contracts or collapses. Such a design is described in U.S. patent application Ser. No. 16/516,416 filed on Jul. 19, 2019, which application is incorporated by reference in its entirety. This similar locking mechanism (i.e., threaded telescoping members) may be used on cross-members 144, 150, 152, 180, and/or 182.

In some embodiments, cross-member 146 comprises an inner rod arranged to slidingly engage an outer rod. The inner rod comprises a plurality of pins and corresponding spring members. The pins protrude from holes in the inner rod, specifically, pins are forced radially outward through the holes in the inner rod by the spring members. The pins may be forced radially inward such that the inner rod can be slid axially within the outer rod. One of the pins is aligned with a hole in outer rod once the desired length of cross-member 146 is achieved. Such a design is described in U.S. patent application Ser. No. 15/678,801 filed on Aug. 16, 2017, which application is incorporated by reference in its entirety. This similar locking mechanism (i.e., the push-pins) may be used on cross-members 144, 150, 152, 180, and/or 182.

Similarly, in some embodiments, at least one of vertical members 140 and 142 comprise a locking and/or control feature. For example, vertical members 140 and/or 142 may comprise a circular geometry and include a threaded telescoping assembly as described above. Alternatively or in addition, vertical members 140 and 142 may comprise the push pin assembly described above.

It should be appreciated that telescoping members are known in the art and that any suitable telescoping design may be used. In an example embodiment, one or more cross-members have a locking or control mechanism. In an example embodiment, no cross-members have a locking or control mechanism. In an example embodiment, one or more vertical members have a locking or control mechanism. In an example embodiment, no vertical members have a locking or control mechanism.

FIGS. 9-11 show elevational views of expandable intervertebral fusion implant 110 in various configurations. Specifically, FIG. 9 shows expandable intervertebral fusion implant 110 in an at least partially or fully collapsed state. As shown, vertical member 140 is at least partially or fully collapsed such that its total length is height H1. Additionally, teeth 166A are substantially engaged with teeth 126A and teeth 172A are substantially engaged with teeth 132A. In the fully collapsed state, longitudinal members 122A, 128A, 162A, and 168A are preferably arranged such that they do not extend further than the ends of vertical member 140 (i.e., longitudinal members 122A, 128A, 162A, and 168A are arranged at an angle less than or equal to 90°). Longitudinal members may be arranged perpendicular to vertical member 140 or at an angle. For example, and as shown in FIG. 9, longitudinal members 122A and 128A are arranged perpendicular to vertical member 140, longitudinal member 162A is arranged angle $\alpha$ relative to vertical member 140 and longitudinal member 168A is arranged at angle $\beta$. In some embodiments, angle $\alpha$ is equal to angle $\beta$ (e.g., angles $\alpha$ and β equal 70°). In some embodiments, angle α is not equal to angle β (e.g., angle α equals 65° and angle β equal 60°). It should be appreciated that longitudinal members 122A, 128A, 162A, and 168A are independently displaceable with respect to each other, and that each can be arranged at different angles relative to vertical member 140. It should further be appreciated that while FIG. 9-11 only depict longitudinal members 122A, 128A, 162A, and 168A and vertical member 140, the same description applies to longitudinal members 122B, 128B, 162B, and 168B and vertical member 142.

FIG. 10 shows expandable intervertebral fusion implant 110 in an expanded state. As shown, vertical member 140 is at least partially or fully collapsed such that its total length is height H1. Longitudinal member 162A has been displaced in circumferential direction CD1 about pivot P2 relative to vertical member 140 and longitudinal member 168A has been displaced in circumferential direction CD2 about pivot P2 relative to vertical member 140. One tooth of teeth 166A is engaged with one tooth of teeth 126A and one tooth of teeth 172A is engaged with one tooth of teeth 132A. In the expanded state shown in FIG. 10, longitudinal members 122A, 128A, 162A, and 168A may extend further than the ends of vertical member 140 (i.e., longitudinal members 122A, 128A, 162A, and 168A may be arranged at an angle greater than or equal to 90°). Longitudinal members may be arranged perpendicular to vertical member 140 or at an angle. For example, and as shown in FIG. 10, longitudinal members 122A and 128A are arranged perpendicular to vertical member 140, longitudinal member 162A is arranged angle α relative to vertical member 140 and longitudinal member 168A is arranged at angle β. In some embodiments, angle α is equal to angle β (e.g., angles α and β equal 110°). In some embodiments, angle α is not equal to angle β (e.g., angle α equals 65° and angle β equal 60°). FIG. 11 shows expandable intervertebral fusion implant 110 in a fully expanded state. As shown, vertical member 140 is fully expanded such that its total length is height 112, which is greater than height H1. Longitudinal member 162A has been displaced in circumferential direction CD1 about pivot P2 relative to vertical member 140 and longitudinal member 168A has been displaced in circumferential direction CD2 about pivot P2 relative to vertical member 140. One tooth of teeth 166A is engaged with one tooth of teeth 126A and one tooth of teeth 172A is engaged with one tooth of teeth 132A. In the expanded state shown in FIG. 11, longitudinal members 122A, 128A, 162A, and 168A generally do not extend further than the ends of vertical member 140 (i.e., longitudinal members 122A, 128A, 162A, and 168A may be arranged at an angle less than or equal to 90°). Longitudinal members may be arranged substantially perpendicular to vertical member 140 or at an angle. For example, and as shown in FIG. 11, longitudinal members 122A, 128A, 162A, and 168A are arranged substantially perpendicular to vertical member 140.

The ability to circumferentially displace each of longitudinal members 122A, 128A, 162A, and 168A, as well as vertical member 140, allows expandable intervertebral fusion implant 110 to be adjusted and expanded in multiple directions, allowing for the optimum disc space to be reached.

Figure 12:
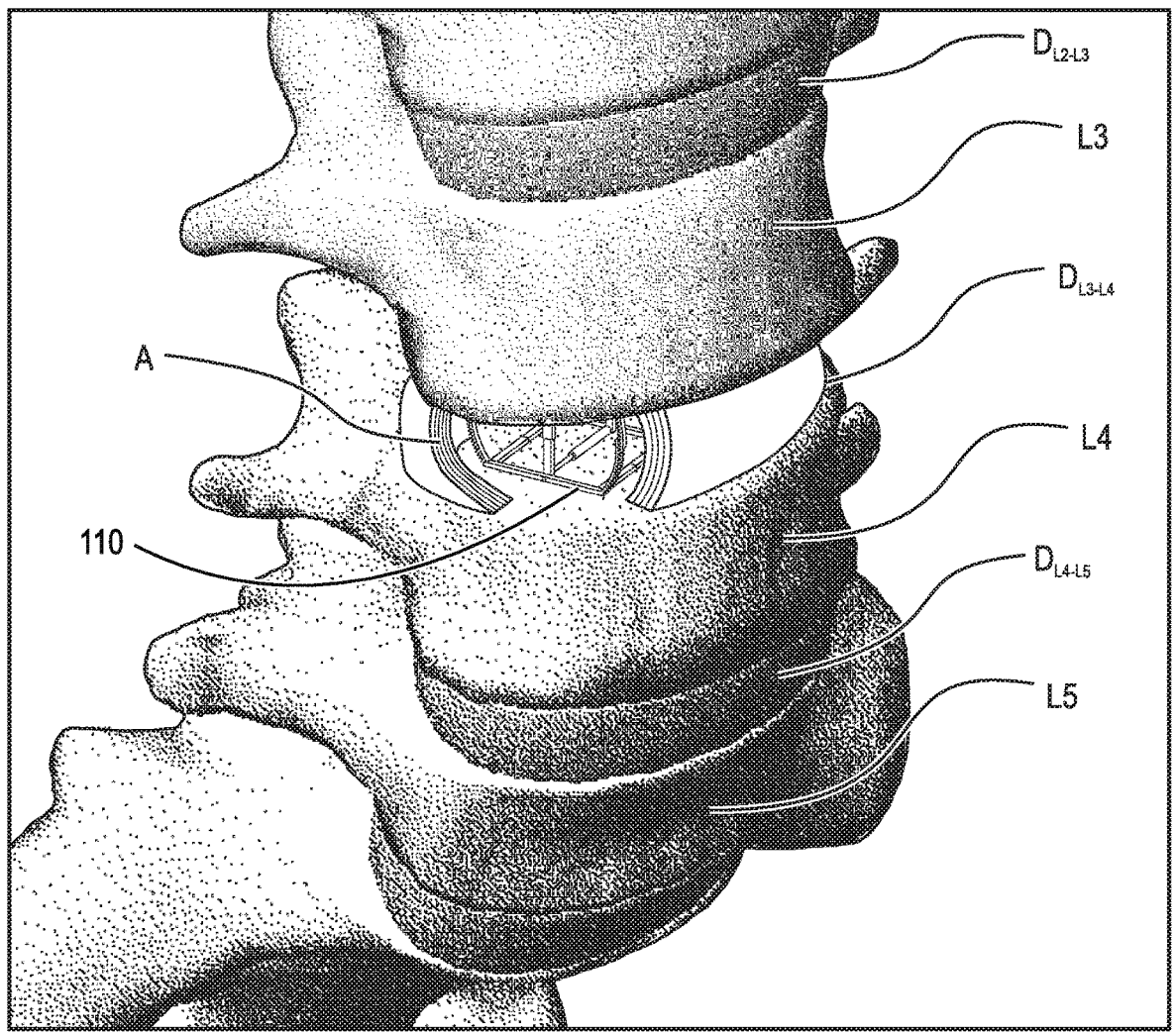

FIG. 12 is an anterior perspective view of a spinal column including the expandable intervertebral fusion implant 110 in the expanded state.

Expandable intervertebral implant 110 is inserted into the spinal column between, for example, the L3 and L4 vertebrae, or where disc $D_{L3-L4}$ should be. Expandable intervertebral implant 110 is then vertically expanded until the desired height is reached. Expandable intervertebral implant 110 may be laterally expanded prior to insertion, or after insertion, as previously discussed (i.e., along telescoping cross-members). Expandable intervertebral implant 110 is then filled with fusion material and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
110 Expandable intervertebral fusion implant
120 Inferior component
122A Longitudinal member
122B Longitudinal member
124A Leg
124B Leg
126A Teeth
126B Teeth
128A Longitudinal member
128B Longitudinal member
130A Leg
130B Leg
132A Teeth
132B Teeth
140 Vertical member
142 Vertical member
144 Cross-member
146 Cross-member
150 Cross-member
152 Cross-member
160 Superior component
162A Longitudinal member
162B Longitudinal member
164A Leg
164B Leg
166A Teeth
166B Teeth
168A Longitudinal member
168B Longitudinal member
170A Leg 170B Leg
172A Teeth
172B Teeth
180 Cross-member
182 Cross-member
P1 Pivot
P2 Pivot
P3 Pivot
P4 Pivot
H1 Height
112 Height
α Angle
β Angle
D1 Direction
D2 Direction
D3 Direction
D4 Direction
CD1 Circumferential direction
CD2 Circumferential direction

What is claimed Is:

1. An expandable intervertebral fusion implant, comprising:
   a first vertical member operatively arranged to extend;
   an inferior component, including:
      first longitudinal member including a first proximal end pivotably connected to the first vertical member and a first distal end; and,
      a second longitudinal member including a second proximal end pivotably connected to the first vertical member and a second distal end, the second distal end being displaceable with respect to the first distal end; and,
   a superior component, including:
      a third longitudinal member including a third proximal end pivotably connected to the first vertical member and a third distal end; and,
      a fourth longitudinal member including a fourth proximal end pivotably connected to the first vertical member and a fourth distal end, the fourth distal end being displaceable with respect to the third distal end;
   wherein the superior component is operatively arranged to displace relative to the inferior component.

2. The expandable intervertebral fusion implant as recited in claim 1, wherein:
   the first longitudinal member comprises a first plurality of teeth;
   the third longitudinal member comprises a second plurality of teeth; and,
   the second plurality of teeth are operatively arranged to engage with the first plurality of teeth.

3. The expandable intervertebral fusion implant as recited in claim 2, wherein the first plurality of teeth and the second plurality of teeth prevent displacement of the first longitudinal member in a first circumferential direction relative to the third longitudinal member.

4. The expandable intervertebral fusion implant as recited in claim 2, wherein:
   the first plurality of teeth are arranged on a first leg extending from the first longitudinal member; and,
   the second plurality of teeth are arranged on a second leg extending from the third longitudinal member.

5. The expandable intervertebral fusion implant as recited in claim 2, wherein:
   the second longitudinal member comprises a third plurality of teeth;
   the fourth longitudinal member comprises a fourth plurality of teeth; and,
   the fourth plurality of teeth are operatively arranged to engage with the third plurality of teeth.

6. The expandable intervertebral fusion implant as recited in claim 5, wherein the third plurality of teeth and fourth plurality of teeth prevent displacement of the fourth longitudinal member in a first circumferential direction relative to the second longitudinal member.

7. The expandable intervertebral fusion implant as recited in claim 6, wherein:
   the third plurality of teeth are arranged on a third leg extending from the second longitudinal member; and,
   the fourth plurality of teeth are arranged on a fourth leg extending from the fourth longitudinal member.

8. The expandable intervertebral fusion implant as recited in claim 1, further comprising:
   a second vertical member connected to the first vertical member via a first cross-member;
   a fifth longitudinal member pivotably connected to the second vertical member; and,
   a sixth longitudinal member pivotably connected to the second vertical member.

9. The expandable intervertebral fusion implant as recited in claim 8, wherein:
   the fifth longitudinal member comprises a first plurality of teeth;
   the sixth longitudinal member comprises a second plurality of teeth; and,
   the second plurality of teeth are operatively arranged to engage with the first plurality of teeth.

10. The expandable intervertebral fusion implant as recited in claim 8, wherein the second vertical member is displaceable relative to the first vertical member.

11. The expandable intervertebral fusion implant as recited in claim 8, wherein the fifth longitudinal member is connected to the first longitudinal member via a second cross-member.

12. An expandable intervertebral fusion implant, comprising:
   a vertical member;
   an inferior component, including:
      first longitudinal member including a first proximal end pivotably connected to the vertical member and a first distal end including a first plurality of teeth; and,
      a second longitudinal member including a second end pivotably connected to the vertical member and a second distal end including a second plurality of teeth, the second distal end being displaceable with respect to the first distal end; and,
   a superior component, including:
      a third longitudinal member including a third proximal end pivotably connected to the vertical member and a third distal end including a third plurality of teeth; and,
      a fourth longitudinal member including a fourth proximal end pivotably connected to the vertical member and a fourth distal end including a fourth plurality of teeth, the fourth distal end being displaceable with respect to the third distal end;
   wherein the superior component is operatively arranged to displace in a first direction relative to the inferior component.

13. The expandable intervertebral fusion implant as recited in claim 12, wherein:
   the third plurality of teeth are operatively arranged to engage the first plurality of teeth; and, the fourth plurality of teeth are operatively arranged to engage the second plurality of teeth.

14. The expandable intervertebral fusion implant as recited in claim 13, wherein the engagement of the third plurality of teeth with the first plurality of teeth and the engagement of the fourth plurality of teeth with the second plurality of teeth prevent displacement of the third and second longitudinal members in a first circumferential direction relative to the first and fourth longitudinal members, respectively.

15. The expandable intervertebral fusion implant as recited in claim 14, wherein the engagement of the third plurality of teeth with the first plurality of teeth and the engagement of the fourth plurality of teeth with the second plurality of teeth prevent displacement of the first and fourth longitudinal members in a second circumferential direction, opposite the first circumferential direction, relative to the third and second longitudinal members, respectively.

16. The expandable intervertebral fusion implant as recited in claim 12, wherein:
   the first plurality of teeth are arranged on a first leg extending substantially perpendicular from the first longitudinal member; and,
   the third plurality of teeth are arranged on a third leg extending substantially perpendicular from the third longitudinal member.

17. The expandable intervertebral fusion implant as recited in claim 16, wherein:
   the second plurality of teeth are arranged on a second leg extending substantially perpendicular from the second longitudinal member; and,
   the fourth plurality of teeth are arranged on a fourth leg extending substantially perpendicular from the fourth longitudinal member.

18. The expandable intervertebral fusion implant as recited in claim 12, wherein the vertical member is operatively arranged to extend in the first direction.

19. The expandable intervertebral fusion implant as recited in claim 18, further comprising a cross-member operatively arranged to expand in a second direction, the second direction being perpendicular to the first direction.

20. An expandable intervertebral fusion implant, comprising:
   a vertical member operatively arranged to extend in a first direction;
   an inferior component, including:
      first longitudinal member pivotably connected to the vertical member and including a first plurality of teeth; and,
      a second longitudinal member pivotably connected to the vertical member and including a second plurality of teeth;
   a superior component, including:
      a third longitudinal member pivotably connected to the vertical member and including a third plurality of teeth; and,
      a fourth longitudinal member pivotably connected to the vertical member and including a fourth plurality of teeth; and,
   a cross-member operatively arranged to expand in a second direction, the second direction being perpendicular to the first direction;
   wherein the superior component is operatively arranged to displace in the first direction relative to the inferior component.

* * * * *